United States Patent [19]

Raabe et al.

[11] 4,020,071
[45] Apr. 26, 1977

[54] DERIVATIVES OF 1-PHENOXY-3-AMINO-PROPAN-2-OL

[75] Inventors: Thomas Raabe, Rodenbach; Otto Gräwinger, Frankfurt am Main; Josef Scholtholt, Mittelbuchen; Rolf-Eberhard Nitz, Bergen-Enkheim; Eckhard Schraven, Frankfurt am Main, all of Germany

[73] Assignee: Cassella Farbwerke Mainkur Aktiengesellschaft, Frankfurt am Main-Fechenheim, Germany

[22] Filed: Dec. 10, 1974

[21] Appl. No.: 531,324

[30] Foreign Application Priority Data

Dec. 20, 1973 Netherlands .................. 7369042

[52] U.S. Cl. .................. 260/256.4 R; 260/240 R; 424/251
[51] Int. Cl.[2] .................. C07D 239/06
[58] Field of Search .............. 260/256.4 R, 240 R; 424/251

[56] References Cited

UNITED STATES PATENTS

| | | | |
|---|---|---|---|
| 3,646,057 | 2/1972 | Beaman et al. | 260/256.4 R |
| 3,686,206 | 8/1972 | Posselt et al. | 260/256.4 R |
| 3,852,291 | 12/1974 | Augstein et al. | 260/256.4 R |

Primary Examiner—Donald G. Daus
Assistant Examiner—James H. Turnipseed
Attorney, Agent, or Firm—Francis M. Crawford

[57] ABSTRACT

The present invention relates to new pharmacologically valuable derivatives of 1-phenoxy-3-amino-propan-2-ol having the formula

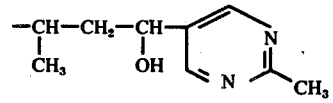

and the aldehyde condensation products and acid addition salts thereof wherein X is selected from the group consisting of

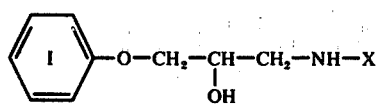

and

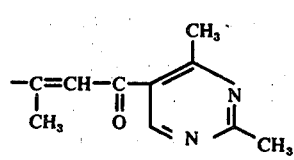

-continued

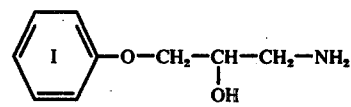

wherein the phenyl ring I may have attached to it up to three similar or different substituents selected from the group consisting of alkyl, alkenyl, alkinyl, cycloalkyl, cycloalkenyl, alkoxy, alkenyloxy, alkinyloxy, benzyloxy, phenyl, halogen and —NR$_1$R$_2$, wherein R$_1$ is selected from alkyl and acyl, and R$_2$ is selected from hydrogen and alkyl; and to the production thereof by a method selected from (A) reacting 1-phenoxy-3-amino-propan-2-ol having the formula

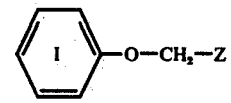

with a compound having the formula Y-X, wherein X has the above-defined meaning and Y is selected from halogen, —OH, —OK or —ONa; (B) reacting a compound of the formula

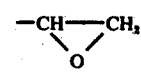

with a compound of the formula H$_2$N—X, wherein X has the above-defined meaning and Z is selected from

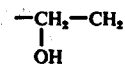

and

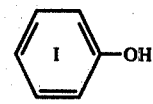

(C) reacting a phenol wherein X and Z have the meaning defined above.

11 Claims, No Drawings

DERIVATIVES OF 1-PHENOXY-3-AMINO-PROPAN-2-OL

The invention relates to new, pharmacologically valuable derivatives of 1-phenoxy-3-aminopropan-2-ol of the general formula I

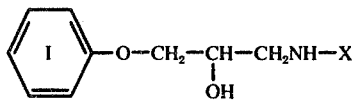

wherein X denotes

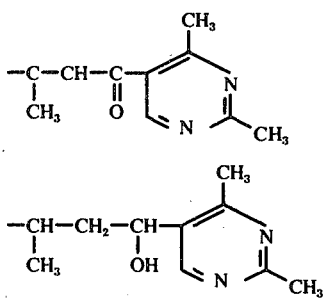

and the phenyl nucleus I can also be mono-substituted, disubstituted or tri-substituted, particularly by alkyl, alkenyl, alkinyl, cycloalkyl, cycloalkenyl, alkoxy, alkenyloxy, alkinyloxy, benzyloxy, phenyl, halogen or the radical $-NR_1R_2$, $R_1$ representing alkyl or acyl and $R_2$ representing hydrogen or alkyl, to aldehyde condensation products and acid addition salts thereof, and to a process for their preparation. The substituents of the phenyl nucleus I can be identical or different.

Compounds having X =
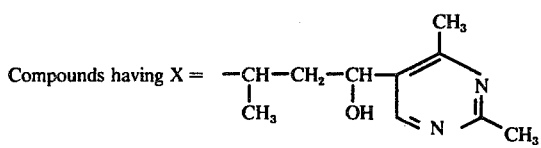

are preferred.

By the compounds of the general formula I, there are also understood, within the scope of the present invention, possible stereoisomers and optically active compounds and mixtures thereof, particularly the racemate.

The substituents of the phenyl nucleus I have, in particular, the following meaning: alkyl having 1 to 4 C atoms, for example methyl, ethyl, propyl or tert.-butyl; alkenyl having up to 6 C atoms, preferably vinyl, allyl, methallyl or crotyl; alkinyl having up to 6 C atoms, for example propargyl; cycloalkyl having a ring size of 5 to 8 C atoms, preferably cyclopentyl and cyclohexyl; cycloalkenyl having a ring size of 5 to 8 C atoms, preferably cyclopentenyl; alkoxy having up to 8 C atoms, or alkenyloxy and alkinyloxy having in each case up to 5 C atoms, preferably methoxy, ethoxy, n-propoxy and i-propoxy, butoxy, n-pentyloxy, n-octyloxy, allyloxy, methallyloxy, propargyloxy or benzyloxy. Halogen: preferably fluorine, chlorine or bromine. Alkyl radicals representing $R_1$ or $R_2$ preferably have 1 to 2 C atoms.

By the acyl radical representing $R_1$ there is understood the aryl-substituted or alkyl-substituted carbonyl radical derived from an aromatic or aliphatic carboxylic acid and having up to 11 C atoms, for example formyl, acetyl, propionyl, butyryl, benzoyl, naphthoyl or phenylacetyl, but preferably acetyl or benzoyl.

The aldehyde condensation products of compounds of the general formula I are oxazolidines of the formula II

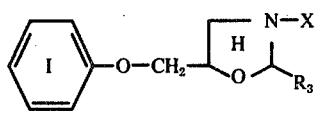

which are formed in the condensation of compounds of the general formula I with an aldehyde of the formula

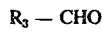

in which $R_3$ represents hydrogen or a lower alkyl radical having up to 4 C atoms.

Inorganic and organic acids are suitable for the formation of salts with the compounds of the general formula I. Examples of suitable acids are hydrogen chloride, hydrogen bromide, phosphoric acid, sulphuric acid, oxalic acid, lactic acid, tartaric acid, acetic acid, salicylic acid, benzoic acid, citric acid, adipic acid or naphthalene-1,5-disulphonic acid. Pharmaceutically acceptable acid addition salts are preferred.

The phenyl nuclei I of the structural formulae which follow can be substituted as indicated above in the case of the general formula I.

In order to prepare the compounds of the general formula I, a 1-phenoxy-3-aminopropan-2-ol of the general formula III is reacted with a compound of the general formula IV with elimination of H—Y to form a compound I according to the invention:

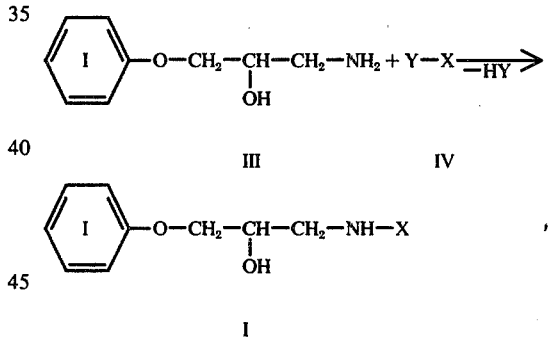

In this, X has the meaning already mentioned and Y denotes halogen, particularly chlorine or bromine, and, if X represents

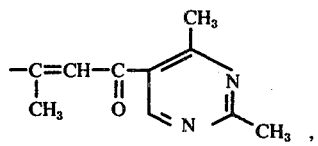

also —OH, —OK or —ONa.

The reaction is normally carried out in a suitable solvent or dispersing agent in which the reactants are dissolved or suspended. Examples of solvents or dispersing agents of this kind are aromatic hydrocarbons, such as, for example, benzene, toluene or xylene; ketones, for example acetone or methyl ethyl ketone; halogenated hydrocarbons, such as, for example, chloroform, carbon tetrachloride, chlorobenzene or methylene chloride; ethers, such as, for example, tetrahydrofurane and dioxane; sulphoxides, such as, for example, dimethylsulphoxide; or tertiary acid amides, such as, for example, dimethylformamide and N-methylphyrrolidone. The solvents used are, in particular, polar solvents, such as, for example, alcohols, Examples of suitable alcohols are methanol, ethanol, isopropanol, tert.-butanol and the like. The reaction is carried out at temperatures from 20° C up to the reflux temperature of the solvent or dispersing agent used. The reaction frequently takes place even at normal temperature.

If X represents

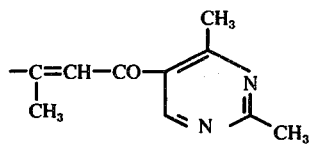

the reaction is accelerated by adding an acid, preferably hydrogen chloride. Examples of other suitable acids are carboxylic acids, such as, for example, formic acid, acetic acid, porpionic acid or butyric acid; sulphonic acids, such as, for example, benzenesulphonic acid and p-toluenesulphonic acid; or mineral acids, such as, for example, sulphuric acid and phosphoric acid. If a compound of the general formula IV having Y = OH is employed, even catalytic amounts of the acid, for example of acetic acid or formic acid, are adequate to accelerate the reaction, If compounds of the general formula IV having Y = ONa or OK are employed, about 1 mol of the acid is added. Instead of adding an acid, it is also possible to accelerate the reaction by employing the compound of the general formula III in the form of a salt, for example the hydrohalide. If a compound of the general formula IV in which Y represents halogen is employed, it is also possible to employ this compound of the general formula IV in the form of the hydrohalide. In the preparative process according to the invention, the acid addition salts of the compound I can be formed, or, on adding an acid-binding agent such as potassium carbonate or sodium carbonate, the free amines can be formed.

Depending on the meaning of X, the starting compounds of the general formula IV which are required are either derivatives of 1-(2,4-dimethyl-5-pyrimidyl)-but-2-en-1-one of the general formula V or of 1-(2,4-dimethyl-5-pyrimidyl)-butan-1-ol of the general formula VI:

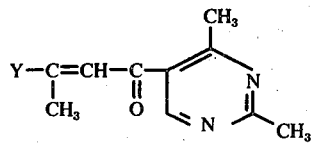

-continued

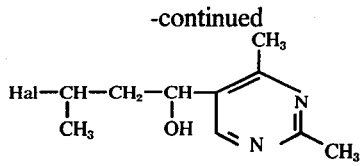

In this, Y has the meaning already indicated and Hal represents halogen, particularly chlorine or bromine. Starting compounds of the general formula V can be obtained, either by reacting a 2,4-dimethylpyrimidine-(5)-carboxylic acid ester, particularly the methyl or ethyl ester, with acetone under the conditions of an alkaline ester condensation, or by reacting an acetic acid ester, particularly methyl or ethyl acetate, under analogous conditions with 2,4-dimethyl-5-acetyl-pyrimidine. This gives the sodium salt or potassium salt of the formula VII or VIII, respectively:

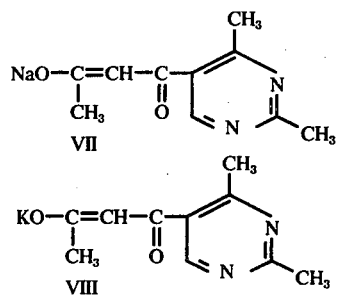

The free 2-dimethylpyrimidoyl-1-methylvinyl alcohol of the formula IX, which is tautomeric with the dimethylpyrimidoyl-acetone of the formula X:

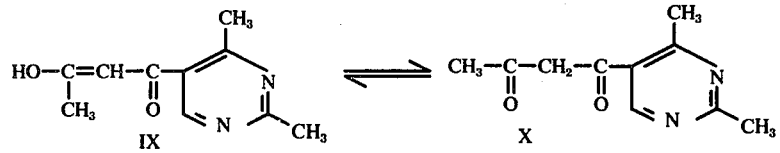

is obtained from these salts by hydrolysis.

By reacting the compound of the formula IX or X with suitable halogenating agents, such as, for example, thionyl chloride or phosphorus tribromide, the corresponding 3-halogeno-1-[2,4-dimethyl-pyrimidyl(5)]-but-2-en-1-one of the general formula XI

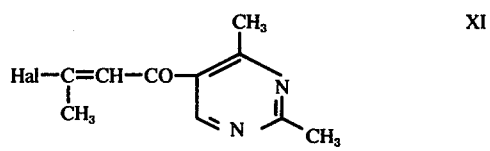

wherein Hal represents halogen, particularly chlorine or bromine, is obtained. Compounds of the general formula VI can be prepared from the corresponding compounds of the formula XI by hydrogenation, appropriately by means of complex hydrides, such as, for example, lithium aluminium hydride, sodium borohydride or the like.

The compounds of the general formula III which are required as starting compounds can be prepared by reacting, with ammonia or with compounds which split off ammonia, a compound of the general formula XII or XIII

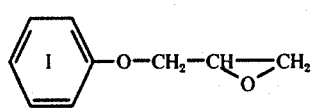

XII

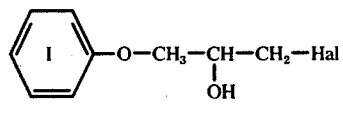

XIII

Hal in XIII denoting a halogen atom, particularly chlorine or bromine, or a mixture of a compound XII with a compound XIII which is identically substituted in the phenyl nucleus I. The reaction can be carried out under atmospheric pressure or under elevated pressure at ambient temperature and can be accelerated or brought to completion by supplying heat, for example by heating to 70° C.

The compounds of the general formulae XII and XIII can be prepared by reacting a phenol of the general formula

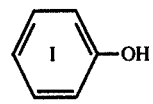

XIV with an epihalogenohydrin, appropriately with epichlorohydrin or epibromohydrin. A compound of the general formula XII or XIII or a mixture of compounds of the general formula XII and XIII is formed in the course thereof, depending on the reaction conditions. The reaction product formed can be isolated before being further reacted with ammonia, but it can also be directly reacted further without isolation.

Compounds of the general formula I can also be prepared by reacting a compound of the general formula XV with a compound of the general formula XVI:

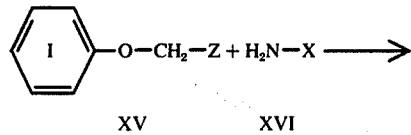

XV    XVI

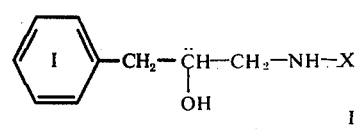

I

In this, X has the meaning already mentioned and Z denotes:

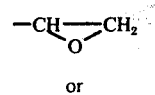

or

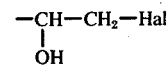

wherein Hal represents a halogen atom, particularly chlorine or bromine.

The reaction is normally carried out in a suitable solvent or dispersing agent in which the reactants are dissolved or suspended. Examples of solvents or dispersing agents of this kind are aromatic hydrocarbons, such as, for example, benzene, toluene or xylene; ketones, such as, for example, acetone or methyl ethyl ketone; halogenated hydrocarbons, such as, for example, chloroform, carbon tetrachloride, chlorobenzene or methylene chloride; ethers, such as, for example, tetrahydrofurane and dioxane; sulphoxides, such as, for example, dimethylsulphoxide; or tertiary acid amides, such as, for example, dimethylformamide and N-methylpyrrolidone. The solvents used are, in particular, polar solvents, such as, for example alcohols. Examples of suitable alcohols are methanol, ethanol, isopropanol, tert.-butanol and the like. The reaction is carried out at temperatures from 20° C up to the reflux temperature of the solvent or dispersing agent used. The reaction frequently takes place at temperatures of 40 to 50° C.

It can be advisable to employ the starting compound of the general formula XVI in a one- to 10-fold molar excess and/or to add the reaction component of the general formula XV in a dissolved or suspended form to the dissolved or suspended reaction component of the general formula XVI. The molar ratio between the compounds of the general formula XV and XVI can be 1 : 1 to 1 : 10 and optionally even more.

In carrying out the reaction, a compound of the general formula XII or of the general formula XIII or a mixture of both these compounds, can be employed as the compound of the general formula XV.

If a compound of the general formula XIII is present, it is also possible to carry out the reaction in the presence of acid-binding agents, such as potassium carbonate, sodium carbonate and the like. Without an acid-binding agent, the hydrohalides of the compounds of the general formula I are usually obtained.

The preparation of the starting compounds of the general formula XVI is described in the examples.

In order to prepare the compounds of the general formula I it is also possible to react a phenol of the general formula XIV with a compound of the general formula XVII to give a compound of the general formula I:

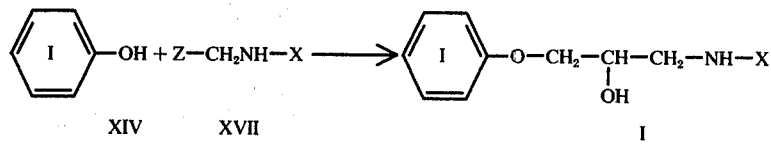

XIV    XVII    I

In this, X has the meaning already mentioned and Z denotes:

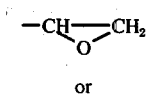

or

-continued

—CH—CH$_2$—Hal
  |
 OH wherein Hal represents a halogen atom, particularly chlorine or bromine.

This reaction too is normally carried out in a suitable solvent or dispersing agent in which the reactants are dissolved or suspended. Examples of solvents or dispersing agents of this kind are aromatic hydrocarbons, such as, for example, benzene, toluene or xylene; ketones, such as, for example, acetone or methyl ethyl ketone; halogenated hydrocarbons, such as, for example, chloroform, carbon tetrachloride, chlorobenzene or methylene chloride; ethers, such as, for example, tetrahydrofurane and dioxane; sulphoxides, such as, for example, dimethylsulphoxide; or tertiary acid amides, such as, for example, dimethylformamide and N-methylpyrrolidone. Polar solvents, in particular, such as, for example, alcohols, are used as the solvent. Examples of suitable alcohols are methanol, ethanol, isopropanol, tert,-butanol and the like. If Z denotes

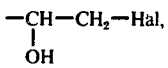

the reaction is generally carried out in the presence of an acid-binding agent, such as, for example, potassium carbonate, sodium carbonate or sodium bicarbonate. The reaction can also be carried out in aqueous alkalis, such as, for example, dilute sodium hydroxide or potassium hydroxide solution. The reaction temperature can be from 20° up to the reflux temperature of the solvent or dispersing agent used.

It can be advisable to employ the starting compound of the general formula XVII in a one- to 10-fold molar excess and/or to add the reaction component of the general formula XIV in a dissolved or suspended form to the dissolved or suspended reaction component of the general formula XVII. The molar ratio between the compounds of the general formula XIV and XVII can be 1 : 1 to 1 : 10 and optionally even more.

In carrying out the reaction it is possible to employ a compound of the general formula XVIII or of the general formula XIX or a mixture of both these compounds, as the compound of the general formula XVII.

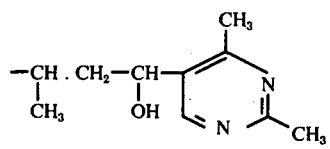

The compounds of the general formula XVIII and XIX can be prepared by reacting a compound of the general formula XVI with an epihalogenohydrin, appropriately with epichlorohydrin or epibromohydrin. A compound of the general formula XVIII or XIX or a mixture of compounds of the general formula XVIII and XIX is formed in the course thereof, depending on the reaction conditions. The reaction product formed can be isolated in order to be reacted further, but it can also be directly reacted without isolation.

The compounds of the general formula I in which X denotes the radical

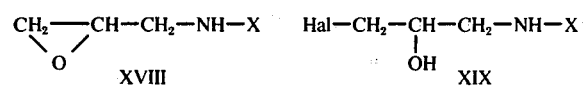

and which therefore have the general formula XX

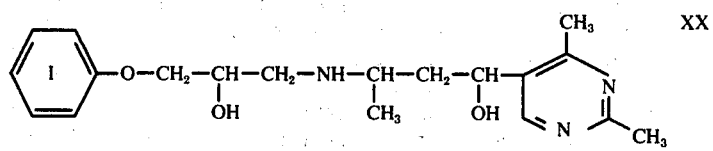

can also be prepared by hydrogenating a compound of the general formula XXI, XXII or XXIII

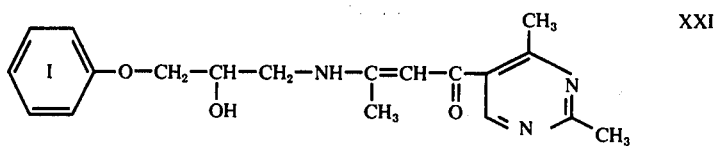

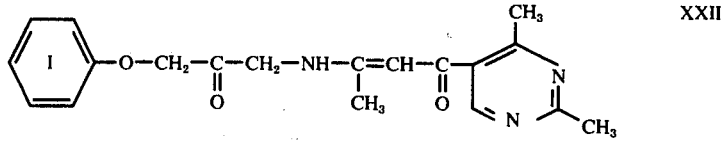

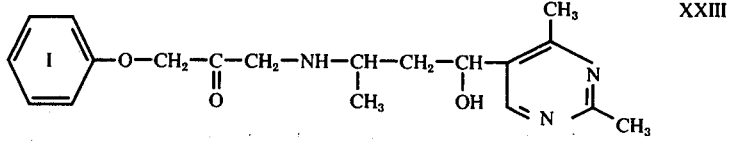

It is advantageous to employ, for the hydrogenation, complex hydrides, such as, for example, lithium aluminium hydride, sodium borohydride and the like. The reaction is carried out under the reaction conditions which are known for these hydrides, normally in alcohol or an alcohol/water mixture at room temperature or elevated temperature, for example while boiling under reflux. In some cases the hydrogenation can also be carried out catalytically, for example using a palladium-charcoal catalyst.

The starting compounds of the general formula XXI are compounds, according to the invention, of the general formula I wherein X represents the radical -continued

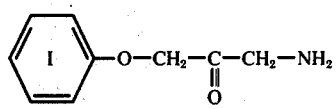

XXIV

Aldehyde condensation products of the formula II are obtained by reacting, in a diluent or solvent, for

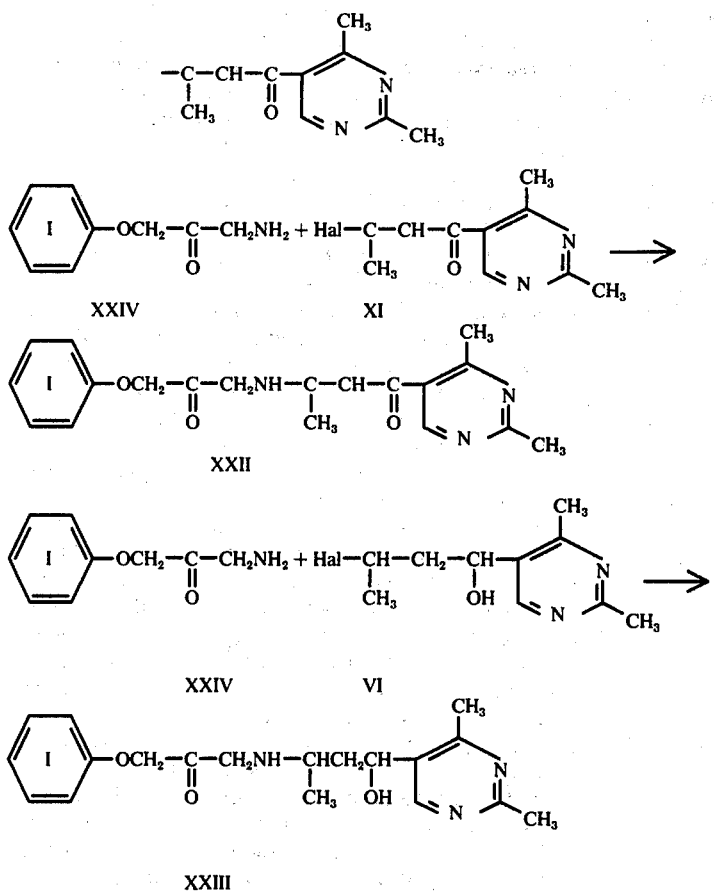

The reaction between the compounds of the general formula XXIV and XI or XXIV and VI, respectively, is carried out in solvents such as benzene, toluene, chloroform, methylene chloride, dioxane and the like, at normal temperature or elevated temperature in the presence of at least molar quantities of an acid-binding agent, such as potassium carbonate or sodium carbonate, or in the absence of acidbinding agents, the hydrohalides of the compounds XXII or XXIII being usually obtained in the latter case.

Compounds of the general formula XXIV can be prepared, for example, by gentle oxidation of the aminopropanols III

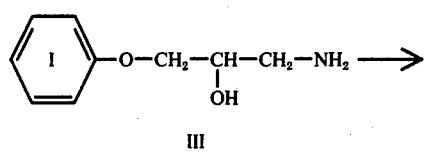

III example ethanol, preferably in the presence of an acid catalyst, for example acetic acid or hydrochloric acid, and preferably at elevated temperature, compounds of the general formula I with an aldehyde of the formula $R_3$-CHO wherein $R_3$ denotes hydrogen or a lower alkyl radical. The water formed in the reaction can be removed by azeotropic distillation with the aid of an entraining agent, for example benzene, or by means of a dehydrating agent, such as anhydrous potassium carbonate.

The acid addition salts of the compounds of the general formula I can be prepared from the components in a manner which is in itself known. The use of a diluent is generally advantageous here, the di-salts of the compounds of the general formula I being generally obtained when there is an excess of acid. The mono-acid addition salts are obtained either by controlled addition of only 1 mol of acid or by partial hydrolysis of the di-acid addition salts.

The compounds of the general formula I, their aldehyde condensation products II and their pharmaceutically acceptable acid addition salts possess valuable pharmaceutical properties. Thus they are suitable, for example, for the treatment of heart diseases. In addition, some of them have very marked β-adrenolytic or anti-arrhythmic properties. The compounds can, therefore, be used as pharmaceutical preparations, on their own, in mixtures with one another or mixed with diluents or excipients which are pharmaceutically unobjectionable. The pharmaceutical preparations can be present in the form of, for example, tablets, capsules, aqueous or oily solutions or suspensions, emulsions, injectable aqueous or oily solutions or suspensions, dispersible powders or aerosol mixtures. Besides the compounds of the general formula I, the pharmaceutical preparations can also contain one or more other pharmaceutically active substances, for example sedatives, such as, for example, Luminal, Meprobamat and Chlorpromazine; vasodilators, such as, for example, glycerol trinitrate and carbochromene, diuretics, such as, for example, chlorothiazide; agents for tonicising the heart, such as, for example, digitalis preparations; hypotension agents, such as, for example, Rauwolfia alkaloids; and broncho-dilators and sympathomimetic agents, such as, for example, Isoprenalin and Ephedrin.

Compounds according to the invention, of the general formula I, which are preferred are those in which X has the meaning:

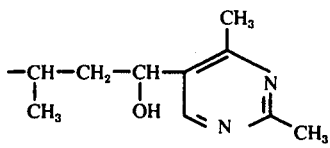

Compounds of the formula:

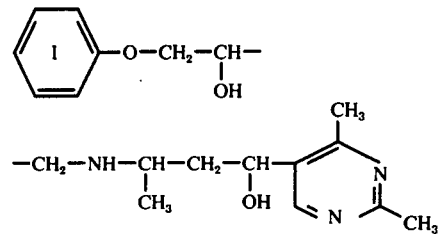

wherein:
the nucleus I is selected from the group of phenyl, chlorophenyl, fluorophenyl, bromophenyl, alkoxyphenyl having 1 to 8 carbon atoms in the alkyl moiety; or their pharmaceutically acceptable acid addition salts are particularly preferred.

The blocking action of the compounds according to the invention on the B1-receptors of the heart and on the B2-receptors of the cardiovascular system was investigated as follows: the blood pressure in the left-hand ventricle was measured on mongrel dogs of both sexes under anaesthesia by Chloralose-urethane-morphine and the pressure signal was continuously differentiated by means of an analogue computer (BRUSH Instruments, Cleveland, Oh.) and, inter alia, the rate of pressure increase (Dp/dt) was recorded. In addition, the perfusion of a femoral artery was measured by means of an electromagnetic flow meter (Model M4000 of Messrs. Statham) and the perfusion was recorded in ml/minutes.

Alterations in the maximum rate of pressure increase (Dp/dt max.) compared with the zero value were induced by intravenous administration of Isoproterenol (0.5 gamma/kg), a known sympathicomimetic agent (B1-reaction), while alterations of the peripheral perfusion, compared with the zero value, were induced by intraarterial administration of Isoproterenol (0.05 gamma/kg) (β2-reaction) (D.DUNLOP and R. G. Shanks: Selective blockade or adrenoceptive beta-receptors in the heart. Brit. J. Pharmac. Chemother. (1968) 32, 201–218).

The substances to be tested for β-receptor blocking were administered intravenously in increasing dosages to the animals which had been anaesthetised and stimulated by means of Isoproterenol, and the quantity of substance was determined at which a 50% inhibition of the two reactions caused by Isoproterenol occurred (ED50). The ED50 values of the β1-receptor inhibition (mg/kg intravenous) and the ED50 values of the β2-receptor inhibition (mg/kg intravenous) are given in the table which follows. In addition, the relative ED 50 values were calculated for both cases, taking as a basis 4-(2-hydroxy-3-isopropylaminopropoxy)-acetanilide, which was employed as a reference substance, the ED 50 values of the latter being made equivalent to 100. The quotient derived from the ED 50 of the β2-receptor inhibition and the ED 50 of the β1-receptor inhibition represents a measure of the cardioselective action of the substances under investigation. The higher this quotient is, the better the cardioselective action. If the quotient of the reference substance 4-(2-hydroxy-3-isopropylamino-propoxy)-acetanilide is made equivalent to 1, the relative factor indicates how much better the cardioselective action of the compound according to the invention is than that of the reference substance.

Furthermore, the relative ED 50 values of the β1-receptor inhibition (column 2 of the table which follows) are a measure of the effectiveness of the substances to be tested. The lower the figures are, the more active the substances, that is to say the smaller the quantity required for the production of the therapeutic effect.

4-(2-Hydroxy-3-isopropylamino-propoxy)-acetanilide, which is employed as the reference substance, is a preparation which is commercially available as β-blocker and which carries the international, unprotected trade name "Practolol".

| Substance under investigation | β1-receptor inhibition ED 50 (mg/kg intravenous) | Relative β1-receptor inhibition (reference substance = 100) | β2-receptor inhibition ED 50 (mg/kg intravenous) | Relative β2-receptor inhibition (reference substance = 100) | Quotient: ED 50β2-receptor inhibition / ED 50β1-receptor inhibition | Quotient, on basis of reference substance = 1 |
|---|---|---|---|---|---|---|
| 1-(2,4-Dimethyl-5-pyrimidyl)-3-(1-[p-n-propoxy-phenoxy]-2-hydroxy-propyl(3)-amino)-butan-1-ol | 0.0036 | 1.5 | 0.48 | 1.8 | 133 | 1.2 |
| 1-(2,4-Dimethyl-5-pyrimidyl)-3-(1-[p-acetamino-phenoxy]-2-hydroxy-propyl(3)-amino)- | | | | | | |

| Substance under investigation | β1-receptor inhibition ED 50 (mg/kg intravenous) | Relative β1-receptor inhibition (reference substance = 100) | β2-receptor inhibition ED 50 (mg/kg intravenous) | Relative β2-receptor inhibition (reference substance = 100) | Quotient: ED 50 β2-receptor inhibition / ED 50 β1-receptor inhibition | Quotient, on basis of reference substance = 1 |
|---|---|---|---|---|---|---|
| butan-1-ol 1-(2,4-Dimethyl-5-pyrimidyl)-3-(1-[p-n-butoxy-phenoxy]-2-hydroxy-propyl(3)-amino)-butan-1-ol | 0.015 | 6.3 | 4.23 | 15.9 | 287 | 2.5 |
| 1-(2,4-Dimethyl-5-pyrimidyl)-3-(-1-[p-n-pentyloxy-phenoxy]-2-hydroxy-propyl(3)-amino)-butan-1-ol | 0.075 | 31.5 | 9.53 | 35.9 | 127 | 1.14 |
| Reference substance: 4-(2-Hydroxy-3-isopropyl-amino-propoxy)acetanilide | 0.020 | 8.4 | 4.53 | 17 | 225 | 2.02 |
| | 0.238 | 100 | 26.505 | 100 | 110 | 1 |

A tablet containing a compound according to the invention and having a total weight of 100 mg can have the following composition, for example:
5 mg of 1-(2,4-dimethyl-5-pyrimidyl)-3-1-[p-acetamino-phenoxy]-2-hydroxy-propyl(3) amino)-butan-1-ol
10 mg of colloidal silicic acid (Aerosil)
72.5 mg of DAB7 lactose
1.5 mg of gelatine
8.5 mg of DAB7 maize starch and
2.5 mg of Mg stearate USPXVIII Depending on the severity of the case to be treated, it is possible, for example, to administer 1 to 2 of these tablets to a patient three times daily.

The preparation of the compounds of the general formula I is illustrated in greater detail in the following examples. The compounds are frequently oils which cannot be distilled, so that in some cases no melting point is shown. However, in all cases the structure indicated has been confirmed by molecular analysis and/or the infrared spectrum or nuclear resonance spectrum.

EXAMPLE 1

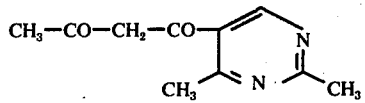

10.6 g of racemic 1-(o-ethoxy-phenoxy)-3-amino-propan-2-ol

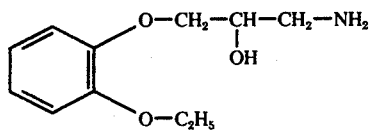

and 100 ml of ethanol are stirred at room temperature for 20 hours. 12.3 g of racemic 1-(2,4-dimethyl-5-pyrimidyl)-3-(1-[o-ethoxy-phenoxy]-2-hydroxy-propyl-3-amino)-but-2-en-1-one of the formula

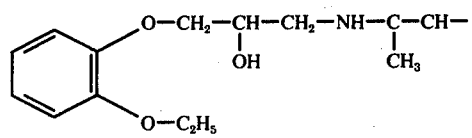

-continued

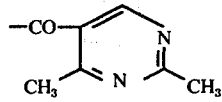

are obtained by filtering the solution, cooled in ice. Melting point: 105°–106°. A further 5.6 g of the substance can be obtained from the filtrate: yield 93% of theory.

Analysis: ($C_{21}H_{27}N_3O_4$)
calculated: C 65.4; H 7.1; N 10.9; O 16.6;
found: C 65.3; H 7.1; N 10.8; O 16.7.

The 2,4-dimethyl-5-pyrimidylcarbonyl-acetone used as the starting substance can be obtained as follows:

222.7 g of 5-acetyl-2,4-dimethylpyrimidine, 5 l of anhydrous toluene, 245 g of methyl acetate and 405 g of potassium tert.-butylate are heated at 60° under nitrogen for 4 hours. The mixture is poured into 2 l of ice water and 205 ml of acetic acid and the toluene solution is separated off and worked up to give 252.3 g of 2,4-dimethyl-5-pyrimidylcarbonyl-acetone, boiling point 112°–118°/0.2 mm Hg, melting point 65°–66° (from ligroin)

Analysis: ($C_{10}H_{12}N_2O_2$)
calculated: C 62.5; H 6.3; N 14.6; O 16.6;
found: O 62.3; H 6.3; N 14.6; O 16.7.

EXAMPLE 2

If, instead of racemic 1-(o-ethoxy-phenoxy)-3-aminopropan-2ol, the laevo-rotatory isomer thereof

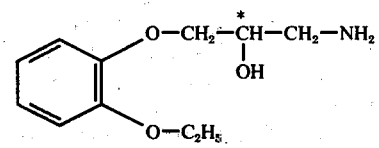

is treated in the same way as described in Example 1, laevo-rotatory (−)-1-(2,4-dimethyl-5-pyrimidyl)-3-(1-[o-ethoxy-phenoxy]-2-hydroxy-propyl-3-amino)-but-2-en-1-one of the formula

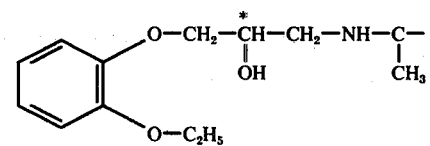

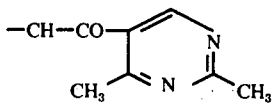

is obtained. Melting point: 103°–105°, $\alpha_D^{25}$: −10°

Analysis: ($C_{21}H_{27}N_3O_4$)

calculated: C 65.4; H 7.1; N 10.9; O 16.6; found: C 65.6; H 7.0; N 11.0; O 16.5.

The laevo-rotatory (−)-1-(o-ethoxy-phenoxy)-3-aminopropan-2-ol used as the starting substance can be prepared from the racemate as follows:

20 g of (o-ethoxyphenoxy)-3-amino-propan-2-ol (racemate) are dissolved in 295 ml of isopropanol and a solution of 7.1 g of L(+)-tartaric acid in 100 ml of isopropanol is added, whereupon a voluminous, white precipitate separates out. The white product is filtered off, washed well with isopropanol and dried in vacuo.

This gives 26.7 g of the tartrate (95% of theory) of 1-(o-ethoxyphenoxy)-3- amino-propan-2-ol having an optical rotation of +12°.

These 26.7 g are recrystallized three times from a mixture of 40 parts of dimethylformamide and 10 parts of water. The tartrate of (−)-1-(o-ethoxyphenoxy)-3-aminopropan-2-ol (2 mols of amine per 1 mol of tartaric acid) having an optical rotation of −1° (melting point 201° C) is finally obtained in this way.

4 g of this salt, finely powdered, are suspended in 60 ml of dioxane and NH₃ gas is passed in at room temperature for ½ hour (the heat of reaction being removed by cooling). Ammonium tartrate is filtered off and the dioxane filtrate is concentrated in vacuo. The solid, white residue is recrystallised from ligroin. This gives laevo-rotatory (−)-1-(o-ethoxyphenoxy)-3-amino-propan-2-ol of melting point 87° C.

Yield = 2.6 g = 88% of theory (calculated on the tartrate of rotation −1°); optical rotation = −5°.

EXAMPLE 3

A mixture of 15.0 g of racemic 1-(2,4-dimethyl-5-pyrimidyl)-3-(1-[o-ethoxy-phenoxy]-2-hydroxy-propyl-3-amino)-but-2-en-1-one of the formula

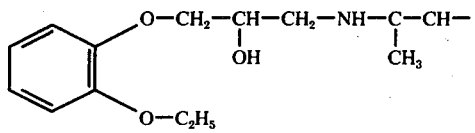

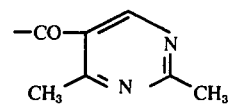

140 ml of ethanol, 50 ml of water and 4.0 g of sodium boranate is heated at 70° for 3 hours and is then evaporated under reduced pressure and the residue is taken up in water and pentan-1-ol. The clear pentanol solution is evaporated again and the residue is thoroughly stirred with ethyl acetate and water at pH 6. The ethyl acetate is discarded and the aqueous solution is adjusted to pH 10 by means of alkali metal hydroxide solution and is once again thoroughly stirred with ethyl acetate. Evaporation of this ethyl acetate gives, as residue, 8.3 g of crude racemic 1-(2,4-dimethyl-5-pyrimidyl)-3-(1-[o-ethoxy-phenoxy]-2-hydroxy-propyl-3-amino)butan-1-ol of the formula

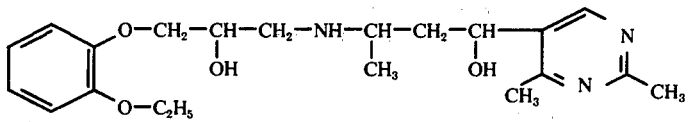

as a viscous oil which can be further purified by column chromatography.

Analysis ($C_{21}H_{31}N_3O_4$)

calculated: C 64.8; H 8.0; N 10.8; O 16.4; found: C 64.5; H 8.1; N 10.7; O 16.6.

If, instead of the abovementioned racemic starting substance, its laevo-rotatory isomer, which can be prepared according to the instruction of Example 2, is used, laevorotatory (−)-1-(2,4-dimethyl-5-pyrimidyl)-3-(1-[o-ethoxyphenoxy]-2-hydroxy-propyl-3-amino)-butan-1-ol of the formula

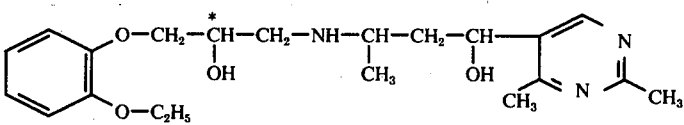

is obtained as a viscous oil, $\alpha_D^{25}$: 1.4°

Analysis: ($C_{21}H_{31}N_3O_4$)

calculated: C 64.8; H 8.0; N 10.8; O 16.4; found: C 64.8; H 7.9; N 10.6; O 16.8.

EXAMPLE 4

A solution of 5.8 g of 2,4-dimethyl-5-pyrimidylcarbonyl-acetone

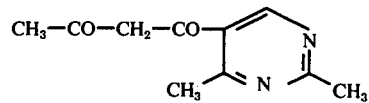

and 7.5 g of 1-(p-n-butoxy-phenoxy)-3-amino-propane-2-ol

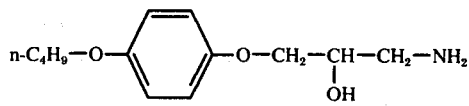

in 50 ml of anhydrous ethanol is allowed to stand for 30 hours at room temperature. It is evaporated under reduced pressure and the residue is crystallised from toluene to give 7.6 g of 1-(2,4-dimethyl-5-pyrimidyl)-3-1-[p-n-butoxy-phenoxy]2-hydroxy-propyl-3-amino)-but-2-en-1-one of the formula

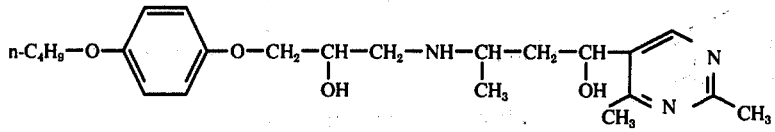

Melting point: 81°–83°. A further 3.3 g of the substance can be obtained from the filtrate.
Analysis: ($C_{23}H_{31}N_3O_4$)
calculated: C 66.8; H 7.6; N 10.1; O 15.5; found: C 66.6; H 7.7; N 10.3; O 15.6.

If this substance is reduced by means of sodium boranate, as described in Example 3, 1-(2,4-dimethyl-5-pyrimidyl)-3-(1-[p-n-butoxy-phenoxy]-2-hydroxy-propyl-3-amino)-butan-1-ol of the formula

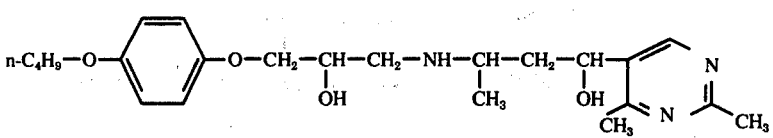

is obtained as a viscous oil.

A solution of this substance in about 5 volumes of ethyl acetate is thoroughly stirred with an aqueous solution of an equivalent quantity of naphthalene-1,5-disulphonic acid. The pure aqueous solution (pH 4) is evaporated and the residue is stirred with anhydrous ether. This gives an 89% yield of the neutral naphthalene-1,5-disulphonate of 1-(2,4-dimethyl-5-pyrimidyl)-3-(1-[p-n-butoxyphenoxy]-2-hydroxy-propyl-3-amino)-butan-1-ol of the formula

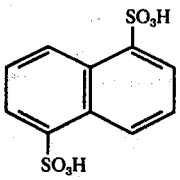

in the form of faintly yellowish crystals, melting point 163°–167° (decomposition).
Analysis: ($C_{28}H_{39}N_3O_7S$)

calculated: C 59.8; H 7.0; N 7.5; O 19.9; S 5.7; found: C 59.7; H 7.0; N 7.3; O 20.2; S 5.8.

EXAMPLE 5

5.6 g of 1-(4-acetamino-phenoxy)-3-amino-propan-2-ol

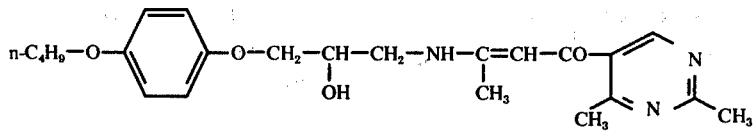

5.3 g of 2,4-dimethyl-5-pyrimidylcarbonyl-acetone

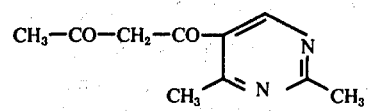

and 50 ml of anhydrous ethanol are heated at 40° for 20 hours. 3.0 g of sodium boranate are introduced in portions at 70° into the reaction mixture and it is heated for a further 7 hours at 70°. It is then evaporated under reduced pressure and the residue is taken up in water and n-pentanol. The pentanol solution is stirred with water and the pH of the latter is adjusted in the course thereof to 6.5 by adding dilute sulphuric acid, and the clear aqueous solution is separated off and once more stirred with n-pentanol at pH 9.5. Evaporating this pentanol solution gives 4.5 g of only slightly contaminated 1-(2,4-dimethyl-5-pyrimidyl)-3(1-[p-acetaminophenoxy]-2-hydroxy-propyl-3-amino)-butan-1-ol of the formula

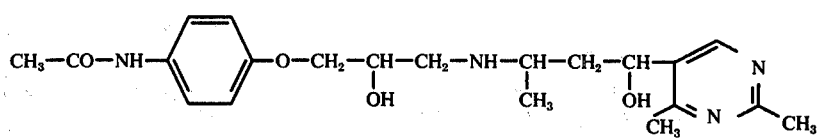

as a viscous oil which can be further purified by column chromatography.
Analysis: ($C_{21}H_{30}N_4O_4$) calculated: C 62.7; H 7.5; N 13.9; O 15.9; found: C 62.4; H 7.5; N 13.7; O 16.2.

0.48 mol equivalent of L-(+)-tartaric acid is added to a solution of the base in ethanol and the reaction mixture is evaporated under reduced pressure and the residue from the above is repeatedly stirred with pure ethyl acetate. This gives white, hygroscopic crystals of the neutral tartrate of 1-(2,4-dimethyl-5-pyrimidyl)-3-(1-[p-acetamino-phenoxy]-2-hydroxy-propyl-3-amino)-butan-1-ol of the formula

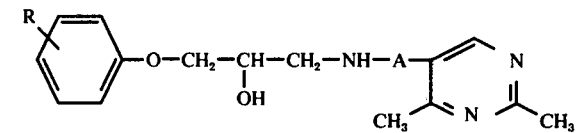

Melting point 83°–87° (decomposition)
Analysis: ($C_{23}H_{33}N_4O_7 \cdot 2H_2O$)
calculated: C 53.8; H 7.3; N 10.9; O 28.0; found: C 53.6; H 7.4; N 10.8; O 28.3.

EXAMPLE 6

The following substances were prepared in a manner identical to that described in Examples 1 to 4:

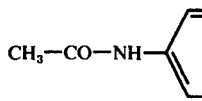
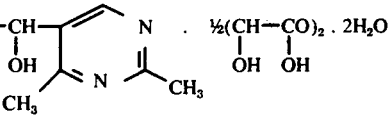

| R | A | |
|---|---|---|
| 2-Cl | —C(CH₃)—CH—CO— | melting point 118–119° |
| 2-Cl | —CH(CH₃)—CH₂—CH(OH)— | oil |
| 4-Cl | —C(CH₃)—CH—CO— | melting point 103–105° |
| 4-Cl | —CH(CH₃)—CH₂—CH(OH)— | oil |
| 4-OCH₃ | —C(CH₃)—CH—CO— | melting point 113–115° |
| 4-OCH₃ | —CH(CH₃)—CH₂—CH(OH)— | oil |
| H | —C(CH₃)—CH—CO— | oil |
| H | —CH(CH₃)—CH₂—CH(OH)— | oil |
| 4-OC₃H₇(n) | —C(CH₃)—CH—CO— | melting point 88–90° |
| 4-OC₃H₇(n) | —CH(CH₃)—CH₂—CH(OH)— | oil |
| 4-OC₃H₇(i) | —C(CH₃)—CH—CO— | melting point 80–82° |
| 4-OC₃H₇(i) | —CH(CH₃)—CH₂—CH(OH)— | oil |
| 2-OCH₃ | —C(CH₃)—CH—CO— | melting point 118–119° |
| 2-OCH₃ | —CH(CH₃)—CH₂—CH(OH)— | oil |
| 3-OC₄H₉(n) | —CH(CH₃)—CH₂—CH(OH)— | oil |
| 3-OC₄H₉(n) | —C(CH₃)—CH—CO— | oil |
| 2-F | —C(CH₃)—CH—CO— | melting point 63–65° |
| 2-F | —CH(CH₃)—CH₂—CH(OH)— | oil |
| 4-OC₈H₁₇(n) | —C(CH₃)—CH—CO— | melting point 68–69° |
| 4-OC₈H₁₇(n) | —CH(CH₃)—CH₂—CH(OH)— | oil |
| 4-C(CH₃)₃ | —C(CH₃)—CH—CO— | melting point 119–120° |
| 4-C(CH₃)₃ | —CH(CH₃)—CH₂—CH(OH)— | oil |
| 3-Cl | —C(CH₃)—CH—CO— | melting point 121–123° |
| 3-Cl | —CH(CH₃)—CH₂—CH(OH)— | oil |
| 3-OCH₃ | —C(CH₃)—CH—CO— | oil |
| 3-OCH₃ | —CH(CH₃)—CH₂—CH(OH)— | oil |
| 4-OC₅H₁₁(n) | —C(CH₃)—CH—CO— | melting point 86–87° |
| 4-OC₅H₁₁(n) | —CH(CH₃)—CH₂—CH(OH)— | oil, naphthalene-1,5-disulphonate (in accordance with Example 4): melting point 202–204° (decomposition) |
| 4-Br | —C(CH₃)—CH—CO— | melting point 65–66° |
| 4-Br | —CH(CH₃)—CH₂—CH(OH)— | oil |
| 4-OC₂H₅ | —C(CH₃)—CH—CO— | melting point 113–115° |
| 4-OC₂H₅ | —CH(CH₃)—CH₂—CH(OH)— | oil |
| 4-OCH₂—C₆H₅ | —C(CH₃)—CH—CO— | melting point 86–87° |
| 4-OCH₂—C₆H₅ | —CH(CH₃)—CH₂—CH(OH)— | oil |

The 1-aryloxy-3-amino-propan-2-ols

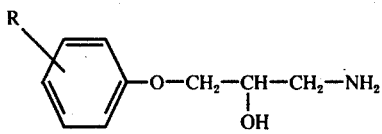

which are used as the starting substances, can be prepared by conventional methods, for example by reacting ammonia with the 1-aryloxy-2,3-epoxypropanes

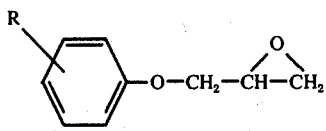

The latter are formed in a known manner from the corresponding phenols ad epichlorohydrin.

The following are thus obtained, for example: 1-(4-n-propoxy-phenoxy)-2,3-epoxy-propane, melting point 43–45°; 1-(4-n-propoxy-phenoxy)-3-amino-propan-2-ol, melting point 99°–101°; 1-(4-i-propoxy-phenoxy)-2,3-epoxy-propane, oil, boiling point 112-115°/0.2 mm Hg; 1-(4-i-propoxy-phenoxy)3-amino-propan-2-ol, melting point 76°–78°; 1-(3-n-butoxyphenoxy)-2,3-epoxy-propane, oil, boiling point 133°–137°/0.1 mm Hg; 1-(3-n-butoxy-phenoxy)-3-amino-propan-2-ol, melting point 59°–60°; 1-(2-fluoro-phenoxy)-2,3-epoxy-propane, oil, boiling point 90°–92°/0.1 mm Hg, 1-(2-fluoro-phenoxy)-3amino-propan-2-ol, melting point 64°–66°; 1-(4-n-octyloxyphenoxy)-2,3-epoxy-propane, melting point 46°–48°; 1-(4-n-octyloxy-phenoxy)-3-amino-propan-2-ol, melting point 106°–107°; 1-(4-benzyloxy-phenoxy)-2,3-epoxy-propane, melting point 55°; 1-(4-benzyloxy-phenoxy)-3-amino-propan-2-ol, melting point 143°–145°; 1-(4-tert,-butyl-phenoxy)-2,3-epoxy-propane, oil, boiling point 110-112°/0.2 mm Hg, 1-(4-tert.-butyl-phenoxy)3-amino-propan-2-ol, melting point 106°–108°; 1-(4-n-pentyloxy-phenoxy)-2,3-epoxy-propane, melting point 37°–38°; and 1-(4-n-pentyloxy)-3-amino-propan-2-ol, melting point 101°–103°.

EXAMPLE 7

2.2 g of 1-(2,4-dimethyl-5-pyrimidyl)-3-(1-[p-nbutoxy-phenoxy]-2-hydroxy-propyl-3-amino)-butan-1-ol of the formula

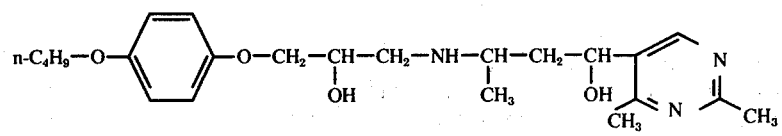

are heated under reflux for 4 hours with 20 ml of ethanol and 0.55 ml of a 39% strength aqueous formaldehyde solution. The reaction mixture is evaporated and the residue is taken up in 200 ml of ligroin. Evaporation of the solution, after clarification by means of a little active charcoal, gives 1.7 g of 3-(1-hydroxy-1-[2,4-dimethyl-5-pyrimidyl]-3-butyl)-5-(4-n-butoxy-phenoxymethyl)oxazolidine of the formula

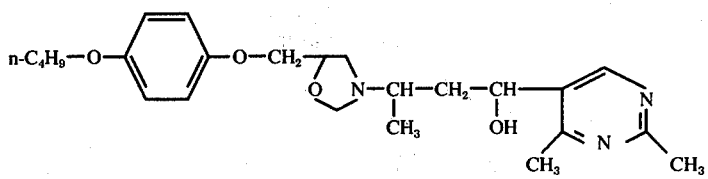

as a colourless oil.
Analysis: $(C_{24}H_{35}N_3O_4)$
calculated: C 67.1; H 8.2; N 9.8; O 14.9; found: C 67.0; H 8.2; N 9.6; O 15.1.

EXAMPLE 8

5.0 g of 1-(2,4-dimethyl-5-pyrimidyl)-3-amino-n-butanol, 50 ml of ethanol (96% strength) and 9.1 g of 1-(4-n-amyloxy-phenoxy)-2,3-epoxy-propane are stirred for 20 hours at room temperature and then heated to 40° C for 3 hours. Evaporation of the reaction mixture in vacuo gives 13.5 g of crude 1-(2,4-dimethyl-5-pyrimidyl)-3-(1-[p-n-amyloxy-phenoxy]-2-hydroxy-propyl-(3)-amino)-butan-1-ol of the formula

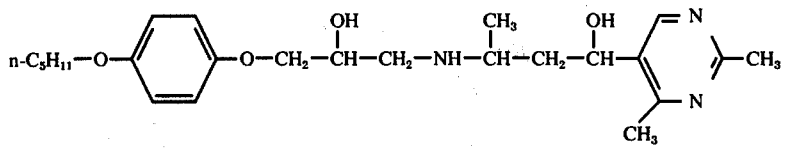

as an oil which is purified further by gel chromatography.
Analysis: $(C_{24}H_{37}N_3O_4)$
calculated C 66.8; H, 8.6; N 9.7; O 14.8; found: C 66.6; H 8.6; N 9.6; O 15.0.

1-(2,4-Dimethyl-5-pyrimidyl)-3-amino-n-butanol, employed above as the starting material, is obtained as follows:

19.6 g of (2,4-dimethyl-5-pyrimidylcarbonyl)-acetone, 200 ml of ethanol and 0.3 g of ammonium bromide are saturated with ammonia at 50° C and heated at 50° C for 20 hours whilst continuing to introduce ammonia.

8.0 g of sodium boranate are introduced in portions over the course of one hour, into the solution, obtained above, of 1-(2,4-dimethyl-5-pyrimidyl)-3-amino-but-2-en-1-one of the formula

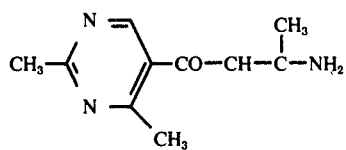

(melting point 93–94°, recrystallised from toluene/ligroin)

and the mixture is stirred for 7 hours at 70° C. The solvent is evaporated off in vacuo and the residue is taken up in aqueous potassium hydroxide solution (20% strength) and 1-pentanol. After working up in the usual manner, 18.5 g of crude 1-(2,4-dimethyl-5-pyrimidyl)-3-amino-n-butanol of the formula

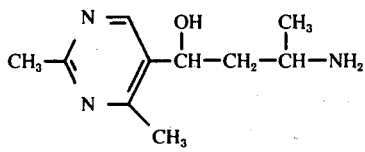

are obtained from the pentanol solution as an oil which can be purified further by column chromatography.

Analysis: ($C_{10}H_{17}N_3O$)

calculated: C 61.5; H 8.8; N 21.5; O 8.2; found: C 61.4; H 8.8; N 21.3; O 8.4.

EXAMPLE 9

8.9 g of 1-(2,4-dimethyl-5-pyrimidyl)-3-chloro-butan-1-ol hydrochloride are introduced in small portions into a suspension of 8.0 g of 1-(4-n-pentyloxy-phenoxy)-3-aminopropan-2-ol (prepared from p-n-pentoxy-phenol and epichlorohydrin, the reaction product then being reacted with ammonia) and 16.0 g of anhydrous potassium hydroxide in 100 ml of anhydrous toluene. The mixture is stirred for 10 hours at room temperature and is then further heated for 5 hours in a waterbath. After cooling, the salt is filtered off and the filtrate is stirred with water and sufficient hydrochloric acid to give a pH of 3 in the aqueous phase. The acid solution is separated from the toluene and washed with ethyl acetate; it is then rendered alkaline with potassium hydroxide and repeatedly extracted with chloroform. Drying and evaporation of the chloroform solution gives 9.3 g of crude 1-(2,4-dimethyl-5-pyrimidyl)-3-(1-[p-n-pentyloxyphenoxy]-2-hydroxy-propyl(3)-amino)-butan-1-ol of the formula

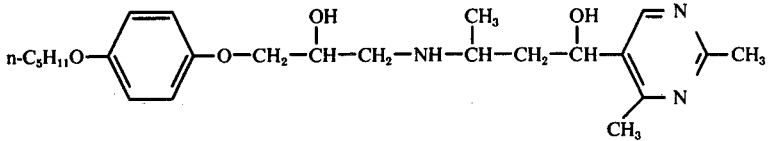

as an oil which is purified further by column chromatography.

Analysis: ($C_{24}H_{37}N_3O_4$)

calculated: C 66.8; H 8.6; N 9.7; O 14.8; found: C 66.7; H 8.6; N 9.6; O 14.9.

1-(2,4-Dimethyl-5-pyrimidyl)-3-chloro-butan-1-ol hydrochloride, used as the starting material, is obtained as follows:

A suspension of the sodium salt of (2,4-dimethyl-5-pyrimidylcarbonyl)-acetone in anhydrous toluene is saturated with hydrogen chloride and then reacted with thionyl chloride in a known manner. Reduction of the reaction product gives 1-(2,4-dimethyl-5-pyrimidyl)-3-chloro-butan-1-ol hydrochloride which is used without additional purification.

What we claimed is:

1. 1-phenoxy-3-amino-propan-2-ol having the structural formula wherein X denotes

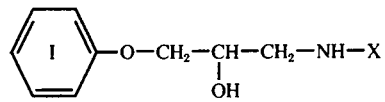

wherein X denotes

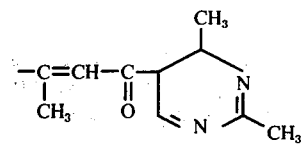

or

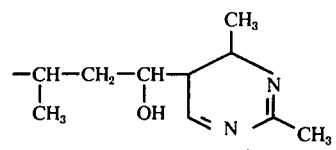

and the phenyl radical I can be mono-, di- or tri-substituted by alkyl having 1 to 4 C atoms, alkenyl having up to 6 C atoms, alkynyl having up to 6 C atoms, cycloalkyl having a ring of 5 to 8 C atoms, cycloalkenyl having a ring of 5 to 8 C atoms, alkoxy having up to 8 C atoms, alkenyloxy having up to 5 C atoms, alkylnyloxy having up to 5 C atoms, phenyl, chlorine or bromine, or the radical —$NR_1R_2$, or wherein $R_1$ represents alkyl having 1 to 4 C atoms or acyl of an aryl or alkyl carboxylic acid having up to 11 C atoms, and $R_2$ represents hydrogen or alkyl having up to 4 C atoms, or a pharmaceutically acceptable acid addition salt thereof.

2. A compound according to claim 1, wherein the phenyl radical I is substituted by a radical selected from the group consisting of vinyl, allyl, methallyl and crotyl.

3. A compound according to claim 1, wherein the phenyl radical is substituted by a cyclopentenyl.

4. A compound according to claim 1, wherein the phenyl radical I is substituted by a substituent selected from the group consisting of cyclopentyl and cyclohexyl.

5. A compound according to claim 1 wherein the phenyl radical I is substituted by a substituent selected from the group consisting of methoxy, ethoxy, propoxy, isopropoxy, butoxy, n-pentyloxy, allyloxy, methallyloxy, propargyloxy and n-octyloxy.

6. A compound according to claim 1, wherein the phenyl radical I is substituted by the radical -$NR_1R_2$, wherein $R_1$ is selected from the group consisting of methyl, ethyl, acetyl and benzoyl, and $R_2$ is selected from the group consisting of hydrogen, methyl and ethyl.

7. A compound of 1-phenoxy-3-amino-propan-2-ol having the structural formula

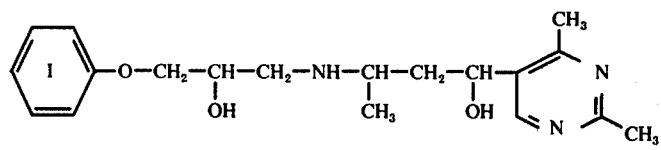

wherein
the nucleus I is selected from the group consisting of phenyl, chlorophenyl, fluorophenyl, bromophenyl, alkoxyphenyl having 1 to 8 carbon atoms in the alkyl moiety, or the pharmaceutically acceptable acid addition salts thereof.

8. The compound having the structural formula

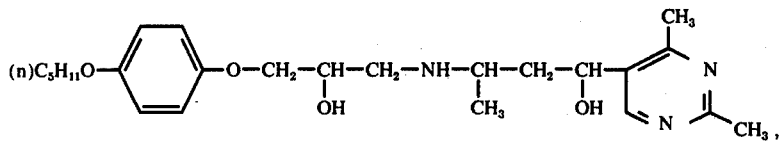

or a pharmaceutically acceptable acid addition salt thereof.

9. The compound having the structural formula

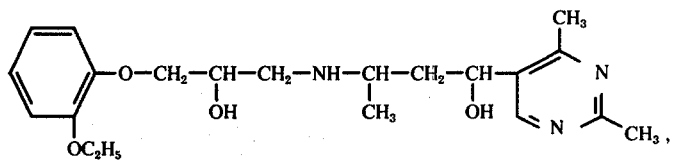

or a pharmaceutically acceptable acid addition salt thereof.

10. The compound having the structural formula

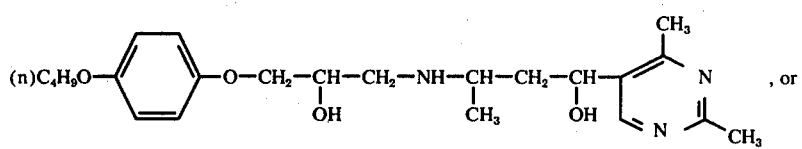

, or a pharmaceutically acceptable acid addition salt thereof.

11. The compound having the structural formula

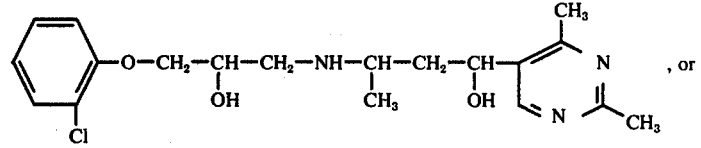

, or a pharmaceutically acceptable acid addition salt thereof.

* * * * *

UNITED STATES PATENT OFFICE
CERTIFICATE OF CORRECTION

Patent No. 4,020,071                    Dated April 26, 1977

Inventor(s) Thomas Raabe et al.

It is certified that error appears in the above-identified patent and that said Letters Patent are hereby corrected as shown below:

Right hand column of the title page, the first formula (line 2) should read:

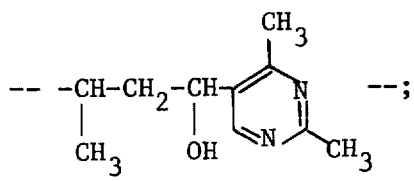

directly below the last formula and before the next line of printed text should read --with $Z-CH_2-NH-X$,--. Column 1, line 27, "disubstituted" should read --di-substituted--. Column 5, line 26, "formula" should read --formula XIV--; Column 12, approximately lines 61 and 62, and Column 14, approximately lines 5 and 6, each occurrence of "$\frac{ED\ 50\beta 2\text{-receptor inhibition}}{ED\ 50\beta 1\text{-receptor inhibition}}$" should read --$\frac{ED\ 50\ \beta 2\text{-receptor inhibition}}{ED\ 50\ \beta 1\text{-receptor inhibition}}$--; Column 13, directly below "EXAMPLE 1" (line 42) and above the first formula of EXAMPLE 1, should read --9.6 g of 2,4-dimethyl-5-pyrimidylcarbonyl-acetone--. Column 14, line 46, "O 62.3;"

UNITED STATES PATENT OFFICE
CERTIFICATE OF CORRECTION

Patent No. 4,020,071  Dated  April 26, 1977

Inventor(s) Thomas Raabe et al.

It is certified that error appears in the above-identified patent and that said Letters Patent are hereby corrected as shown below:

should read --C 62.3;--. Column 26, line 3 of claim 10, delete ", or"; line 3 of claim 11, delete ", or".

Signed and Sealed this

Third Day of January 1978

[SEAL]

Attest:

RUTH C. MASON  
Attesting Officer

LUTRELLE F. PARKER  
Acting Commissioner of Patents and Trademarks